United States Patent [19]
Rost

[11] Patent Number: 6,158,889
[45] Date of Patent: Dec. 12, 2000

[54] RHEUMATISM SCANNER WITH HOLDER FOR IMMOBILIZING A FINGER JOINT

[75] Inventor: Helmut Rost, Uttenreuth, Germany

[73] Assignee: Siemens Aktiengesellschaft, Munich, Germany

[21] Appl. No.: 09/280,630

[22] Filed: Mar. 29, 1999

[30] Foreign Application Priority Data

Mar. 30, 1998 [DE] Germany .......................... 198 14 103

[51] Int. Cl.[7] ....................................................... H05G 1/00
[52] U.S. Cl. ........................ 378/208; 378/177; 378/180; 378/195; 601/133
[58] Field of Search ................................ 378/167, 177, 378/180, 195, 208; 128/878, 882, 845; 601/133

[56] References Cited

U.S. PATENT DOCUMENTS

| | | |
|---|---|---|
| 3,639,764 | 2/1972 | Olson et al. . |
| 3,715,587 | 2/1973 | Burkhalter et al. . |
| 4,674,110 | 6/1987 | Eaton et al. . |
| 4,982,744 | 1/1991 | Stanec . |
| 5,323,786 | 6/1994 | Juhasz . |
| 5,327,912 | 7/1994 | Mally . |
| 5,712,892 | 1/1998 | Weil et al. ................................ 378/54 |
| 5,881,730 | 3/1999 | Burger . |
| 6,059,454 | 5/2000 | Masson . |

*Primary Examiner*—David V. Bruce
*Assistant Examiner*—Pamela R. Hobden
*Attorney, Agent, or Firm*—Schiff Hardin & Waite

[57] ABSTRACT

A rheumatism scanner has a hand rest arranged between a radiation source and a detector unit and a holder for immobilizing the examined finger joint on the hand rest. The holder is a finger sled which can be fastened to the finger joint at a location remote from the hand rest, and thus remote from the rest of the scanner, and which is provided with a continuous joint recess. After a finger is fixed in the finger sled the finger sled can be brought into engagement with, and positioned exactly at, the hand rest by adjusting and/or fixing elements.

12 Claims, 2 Drawing Sheets

RHEUMATISM SCANNER WITH HOLDER FOR IMMOBILIZING A FINGER JOINT

BACKGROUND OF THE INVENTION

1. Field of the Invention

The present Invention relates to a rheumatism scanner of the type having a hand rest that is arranged between a radiation source and a detection unit and with a holding unit for immobilizing a finger joint to be examined on the hand rest.

2. Description of the Prior Art

The examination of joints of the finger With a rheumatism scanner has posed considerable problems and has been extremely time-consuming, regardless of the radiation source used to conduct the examination. Experience has shown that a typical rheumatic patient cannot keep his or her hand still, so that immobilization of the joint over the period of the exam is very important. Conventionally, the finger joint is usually fixed on a hand rest by fastening the fingers with the aid of clamping bands. These provide an unsatisfactory and unreliable fastening, however. Furthermore, the distance from the fingertip to the lower finger joint must be measured with a sliding gage before every scan, and the measurement value must be entered into the PC, so that, given placement of the finger at a detent on the hand rest, the exact examination in the joint gap will actually occur. Subsequent to the entry of the measurement value and the fixing of the finger, a step motor extends the positioned joint gap relative to an optical measuring axis. Each finger must be so measured and positioned with the step motor. This leads to very long examination times and to an equally long occupation of the rheumatologist, who must perform the measuring, the positioning and the examination.

SUMMARY OF THE INVENTION

It is an object of the present invention is to a rheumatism scanner of the above general type which allows a considerably simpler and faster examination and wherein the danger of a blurring of the projections due to twitching movements of the patient is reliably reduced.

This object is achieved in accordance with the invention in a rheumatism scanner having a holder with a finger sled with a continuous joint recess, the sled being fastened at the finger joint and exactly positionable at the hand rest by adjusting and/or fixing elements.

With the inventive design, the finger sled can be fastened to the finger joint to be examined by the medical technician even before the actual rheumatism examination. Only when this preparation is completed and the finger is fixed at the finger sled in a precise orientation does the positioning on the hand rest of the rheumatism scanner occur, which does not entail any more measuring outlay or adjustment at all. The adjustment of the joint gap to a position marker at the finger sled, which due to the amount of time it takes can add to the cost of the examination, occurs outside the rheumatism scanner, so that the actual examination work is not obstructed or prolonged by the time-consuming adjustments. Many more examinations with the aid of a rheumatism scanner can thus be conducted within a unit of time compared to a procedure wherein each joint must itself be individually adjusted at the rheumatism scanner, as previously. In complete examinations in which all the joints of both hands are examined, for example, in accordance with the invention a finger sled can be provided in every other finger, so that six joints can be examined in the rheumatism scanner very rapidly in succession in one examination pass. The six finger sleds being used are subsequently moved onto other joints, and an examination pass for six joints can again occur successively and without an adjustment at the rheumatism scanner.

It is particularly advantageous to provide the finger sled with finger clamps that can be swivelled against the fastened finger from both sides, with two pairs of such finger clamps being swivelled in common toward the finger, these pairs being respectively arranged on opposite sides of a finger joint. In the simplest case, these finger clamp pairs can pivot against each other by means of a clamping screw and enable a very simple, rapid and careful fixing of a finger joint on the finger sled. In addition, a removable soft rubber or plastic sleeve can be provided on each finger clamp in order to avoid painful pressure despite relatively strong fixing of the finger joint.

In another embodiment of the Invention, the finger sled is provided with runners at its underside which are essentially triangular in cross-section and which engage in correspondingly shaped slots of the hand rest, in order to achieve the substantially correct positioning on the hand rest by the mere placement in the hand rest of the finger sled that is fixed at the finger joint to be examined. The actual scanning examination thus can begin almost immediately after the placement of the finger sled on the hand rest.

In a further embodiment of the invention, the finger sled can be displaceable in the slot(s) of the hand rest by means of a laterally engaging displacement device. In this case, a displacement of the radiation source and/or of the radiation detector is not required in order to scan the joint gap; rather, the joint gap is displaced in the radiation beam path by moving the finger sled.

Displacement means for the radiation source and the detector, however, usually are provided already. This in turn enables the possibility of providing a design in which the finger sled has two crossing runners for displacement-free engagement in a cross-slot of the hand rest. This further reduces the examination outlay because only the placement of the finger sled onto the hand rest and the locking of the runners into the slots need to be done. This type of fixing will suffice in most cases.

In another embodiment of the invention, a detachable locking arrangement which prevents the finger sled from raising from the hand rest can be provided. The locking arrangement can, for example, include electromagnets, actuated by remote control, which are arranged in the hand rest in order to lock the finger sled, which contains or is composed at least partially of magnetic material. In this embodiment, the procedure which must be performed at the rheumatism scanner in order to perform a measurement is extremely simplified. The finger sled with its crossing runners is simply inserted into the cross-slot of the hand rest, and the electromagnet is then actuated. In this case, there is an absolutely displacement-free and blur-free immobilization of the finger joint. All the necessary time-consuming adjustment tasks, namely the fixing of the finger joint exactly with respect to the markers at the finger sled, can be performed outside the rheumatism scanner by assistants, and there is no need to occupy the valuable time of the rheumatologist.

Preferably the finger sled is a plastic part, preferably one produced by injection molding, in which iron powder is embedded. The embedded iron powder imparts the magnetic properties for mechanical locking, and the plastic part can be sterilized rather easily.

DESCRIPTION OF THE PREFERRED EMBODIMENTS

Figure 1:
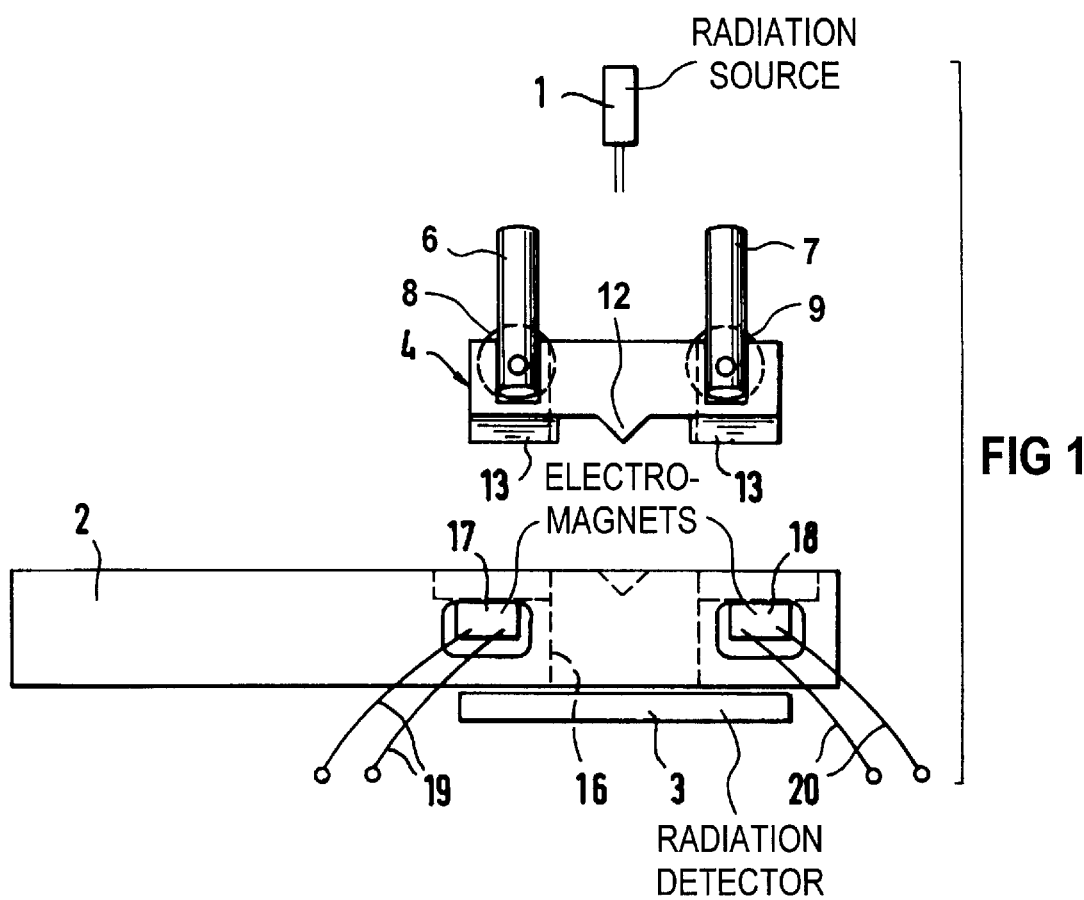
FIG. 1 is a schematic side view of the basic parts of a rheumatism scanner with an inventive finger sled.
Figure 2:
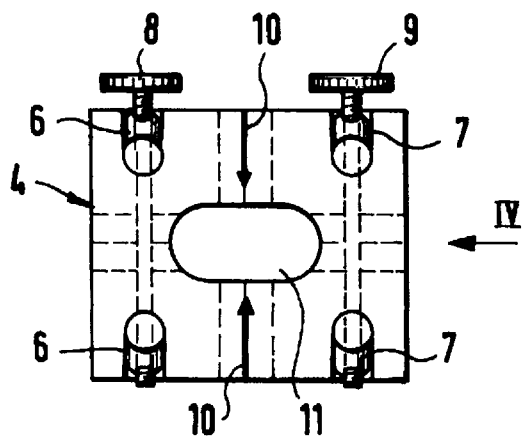
FIG. 2 is a plan view of the inventive finger sled, with inwardly tilted finger clamps.
Figure 3:
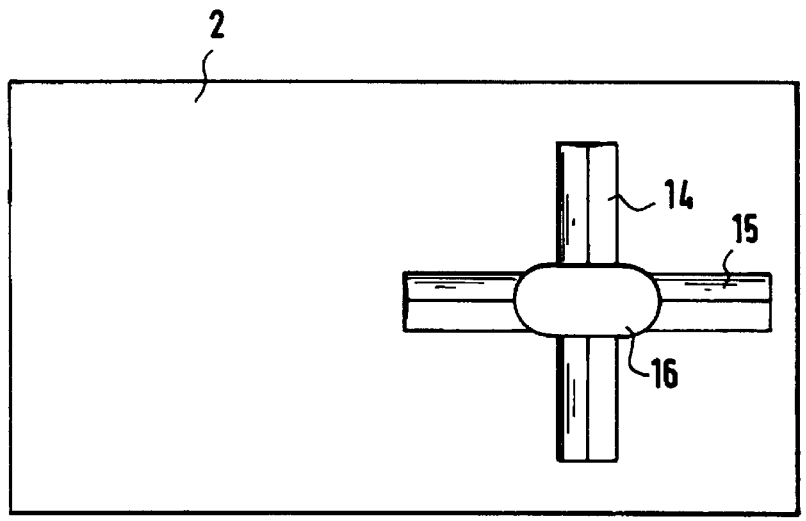
FIG. 3 is a plan view of the hand rest of the rheumatism scanner in FIG. 2.
Figure 4:
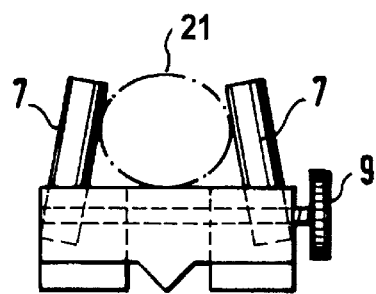
FIG. 4 is a view of the finger sled in the direction of the arrow IV in FIG. 2.

FIG. 1 depicts a rheumatism scanner having a radiation source 1, which is arranged above a hand rest 2, beneath which a detector 3, which is depicted schematically, is disposed. A finger sled 4 is provided to immobilize the finger joint to be examined on the hand rest 2. The sled 4 is equipped with two pairs of finger clamps 6 and 7. The clamps 6 in one pair can be pivoted toward each other by a clamping screw 8 which is threaded through both clamps 6, and the clamps 7 and the other pair can be pivoted toward each other by a clamping screw 9 which is threaded through both clamps 7, in order to fasten an intermediately placed finger. The finger is placed such that the finger clamp pairs 6 and 7 engage above and below the joint, the arrow markers 10 serving for the precise adjustment to the joint gap. In the region of the supported joint, the finger sled is provided with a recess 11, through which the radiation from the radiation source 1 can reach the detector 3 through the joint gap. The exact positioning and fixing of a finger in the finger sled 4 is performed outside the rheumatism scanner by a medical technician. The rheumatologist who conducts the actual scanner exam need not participate at all in that procedure.

In the exemplary embodiment depicted in the FIGS. 1 to 4, an arrangement of two perpendicularly crossing runners 12 and 13 each having a triangular cross-section, is fashioned on the underside of the finger sled 4. Accordingly, the hand rest 2 is provided with correspondingly shaped cross-slots 14 and 15 on the top side. It is also to dispose the two perpendicularly crossing runners on the hand rest and the correspondingly shaped cross-slots in the finger sled. The placement of the finger sled 4 with the fixed finger onto the hand rest 2 by means of engagement in the cross-slots 14 and 15 results in an exact positioning of the joint gap with respect to the beam axis of the scanner, the hand rest being provided with a recess 16 corresponding to the recess 11 of the finger sled. Electromagnets 17 and 18 are embedded in the hand rest 2, which are actuated via schematically depicted power cables 19 and 20, so that the finger sled 4, which is magnetic, can be magnetically locked by exciting the electromagnets 17 and 18, so that the sled cannot be lifted from the hand rest. The rheumatologist can actuate the locking electromagnets 17 and 18 from the operating desk of the rheumatism scanner by remote control. Aside from the simple straight design of the finger clamps which is depicted in the figures, these can also be provided with inwardly inclined upper portions in order to achieve a better fixing of the finger 21. The exact design of the finger clamps, which may additionally be provided with a sterilizeable sleeve, and the exact design of the clamping means, which is indicated only schematically as a through-extending clamping screw, can of course can be modified in a variety of ways.

Figure 5:
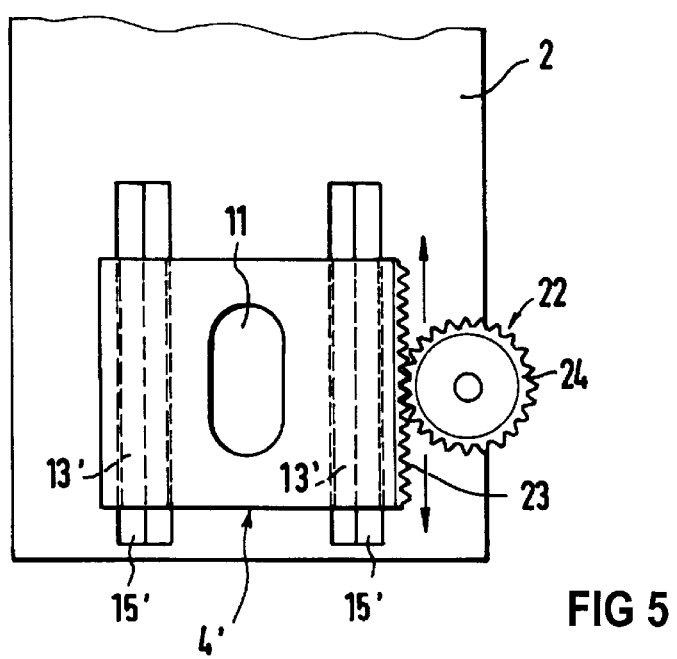
FIG. 5 is a schematic plan view of another embodiment of a rheumatism scanner with finger sleds that can be moved on the hand rest in motorized fashion.

FIG. 5 depicts a modified embodiment wherein the finger sled 4' is provided with two parallel runners 13 prime (instead of crossing runners), which engage in two parallel slots 15' of the hand rest 2. A motorized displacement mechanism 22, which is depicted in the exemplary embodiment by a toothed gear wheel 24 that engages in a toothed rack 23, engages the finger sled 4' laterally, in order to be able to displace the joint gap of the finger into a desirable position by motor operation. In this case, too, the finger is of course fixed at the finger sled 4' outside the actual rheumatism scanner, clamping fingers 6, 7 which are not illustrated in FIG. 5 for clarity, serving this purpose.

The invention is not limited to the depicted exemplary embodiments. Besides an alternatively constructed clamping arrangement for fastening the finger 21 at the finger sled 4, 4', the locking of the finger sled at the hand rest 2 or its longitudinal displacement analogously to the arrangement according to FIG. 5, can occur differently. The material selection for the finger sled also permits a number of variations, the preferred selection being a plastic with embedded iron powder, due to the simple sterilization possibilities, along with a simultaneous capability for magnetic locking at the hand rest 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. In a rheumatism scanner having a radiation source and a radiation detection unit and a holder disposed between said radiation source and said radiation detection unit for immobilizing a finger joint during scanning using said radiation source and said radiation detection unit, the improvement of said holder comprising:

a hand rest;

a finger sled adapted for fastening to a finger joint and having a continuous joint recess therein adapted to receive said finger joint; and at least one engagement element allowing releasable engagement of said finger sled on, and exact positioning of said finger sled relative to, said hand rest.

2. The improvement of claim 1 wherein said finger sled comprises a plurality of finger clamps, disposed on opposite sides of said continuous joint recess, said clamps being pivotable toward said continuous joint recess for fixing said finger joint therebetween.

3. The improvement of claim 2 wherein said plurality of finger clamps comprise a first pair of finger clamps positioned relative to said continuous joint recess to be disposed at a first side of a finger joint in said continuous joint recess, said first pair of finger clamps being pivotable toward said continuous joint recess in common, and a second pair of finger clamps positioned relative to said continuous joint recess to be disposed at a second side of a finger joint in said continuous joint recess, said second pair of finger clamps being pivotable in common toward said continuous joint recess.

4. A rheumatism scanner as claimed in claim 3 further comprising a first clamping screw threadably engaging said first pair of finger clamps for pivoting said first pair of finger clamps in common, and a second clamping screw threadably engaging said second pair of finger clamps for pivoting said second pair of finger clamps in common.

5. A rheumatism scanner as claimed in claim 1 wherein said engagement element comprises a runner projecting from a bottom of said finger sled, said runner having a cross-section, and a channel in a top of said hand rest, said channel having said cross-section and slidably receiving said runner therein.

6. The improvement of claim 5 wherein said cross-section comprises a triangular cross-section.

7. The improvement of claim 5 further comprising a displacement mechanism disposed at a side of said finger sled and engaging said side of said finger sled for displacing said finger sled as said runner slides in said channel.

8. The improvement of claim 5 wherein said projection comprises a first projection and wherein said channel comprises a first channel, and further comprising a second projection disposed on said bottom of said finger sled substantially perpendicular to said first projection, and a second channel in said top of said hand rest, disposed substantially perpendicular to said first channel, said second channel slidably receiving said second projection therein.

9. The improvement of claim 1 further comprising an activatable locking arrangement which, when activated, prevents lifting of said finger sled from said hand rest.

10. The improvement of claim 9 wherein said finger sled is comprised at least in part of magnetic material, and wherein said locking arrangement comprises at least one remotely activatable electromagnet disposed in said hand rest for, when activated, magnetically locking said finger sled to said hand rest.

11. The improvement of claim 10 wherein said finger sled is comprised of plastic having iron powder embedded therein.

12. The improvement of claim 1 further comprising at least one mark on said finger sled for orienting a joint gap of said finger joint relative to said finger sled.

* * * * *